United States Patent
Kawaguchi et al.

(10) Patent No.: US 9,836,937 B2
(45) Date of Patent: Dec. 5, 2017

(54) SENSOR SYSTEM, SENSOR, AND DETACHMENT TOOL

(75) Inventors: Koichiro Kawaguchi, Tokyo (JP); Masashi Arikawa, Tokyo (JP)

(73) Assignee: Hochiki Corporation, Tokyo (JP)

( * ) Notice: Subject to any disclaimer, the term of this patent is extended or adjusted under 35 U.S.C. 154(b) by 665 days.

(21) Appl. No.: 14/383,278

(22) PCT Filed: Aug. 1, 2012

(86) PCT No.: PCT/JP2012/069590
§ 371 (c)(1),
(2), (4) Date: Sep. 5, 2014

(87) PCT Pub. No.: WO2013/157153
PCT Pub. Date: Oct. 24, 2013

(65) Prior Publication Data
US 2015/0030375 A1  Jan. 29, 2015

(30) Foreign Application Priority Data

Apr. 17, 2012  (JP) .................................. 2012-093698

(51) Int. Cl.
*G08B 17/113* (2006.01)
*G01N 21/53* (2006.01)
(Continued)

(52) U.S. Cl.
CPC ........... *G08B 17/107* (2013.01); *G01D 11/30* (2013.01); *G01N 21/53* (2013.01); *G08B 17/113* (2013.01);
(Continued)

(58) Field of Classification Search
CPC .. G01D 11/30; G01N 21/53; G01N 2201/061; G08B 17/113; G08B 17/107; G08B 17/10; Y10T 403/1666
(Continued)

(56) References Cited

U.S. PATENT DOCUMENTS 4,074,341 A   2/1978  Niederost et al.
5,612,678 A   3/1997  Shibata
(Continued)

FOREIGN PATENT DOCUMENTS

JP    09-293181 A    11/1997
JP    2000-268268 A   9/2000
(Continued)

OTHER PUBLICATIONS

Japanese Patent Office, International Search Report issued in corresponding International Patent Application No. PCT/JP2012/069590 and English-language translation (Sep. 11, 2012) (4 pages).
(Continued)

*Primary Examiner* — J M Saint Surin
(74) *Attorney, Agent, or Firm* — Wood Herron & Evans LLP

(57) ABSTRACT

This sensor system includes: a sensor that is provided with a sensor cover having an opening formed on one end and a sensor main body which is detachably disposed on an inner portion of the sensor cover; and a detachment tool used to detach the sensor main body from the sensor cover, wherein the sensor includes an attachment structure used to attach the sensor main body to the inner portion of the sensor cover, the detachment tool includes a detachment structure used to detach the sensor main body from the inner portion of the sensor cover, and in the detachment structure, by pushing the detachment tool into the sensor main body from the opening of the sensor cover, the sensor main body is detached from the inner portion of the sensor cover.

6 Claims, 17 Drawing Sheets

(51) Int. Cl.
  *G01D 11/30* (2006.01)
  *G08B 17/107* (2006.01)
  *G08B 17/10* (2006.01)

(52) U.S. Cl.
  CPC ........ *G01N 2201/061* (2013.01); *G08B 17/10* (2013.01); *Y10T 403/1666* (2015.01)

(58) Field of Classification Search
  USPC .......................................................... 73/431
  See application file for complete search history.

(56) References Cited

U.S. PATENT DOCUMENTS

| | | | |
|---|---|---|---|
| 6,931,898 B2* | 8/2005 | Wendt | E05B 19/20 70/394 |
| 7,426,876 B2* | 9/2008 | Takaku | B23Q 17/003 73/862.21 |
| 7,888,780 B2* | 2/2011 | Anderson | H01L 21/845 257/255 |
| 9,415,452 B2* | 8/2016 | Ueda | B23Q 3/12 |
| 2002/0079412 A1 | 6/2002 | Pitlor | |

FOREIGN PATENT DOCUMENTS

| | | |
|---|---|---|
| JP | 2003-248876 A | 9/2003 |
| JP | 2006267128 A | 10/2006 |

OTHER PUBLICATIONS

European Patent Office, Extended Search Report issued in corresponding European Patent Application No. 12874704.5 dated Jul. 22, 2015.

* cited by examiner

FIG. 11
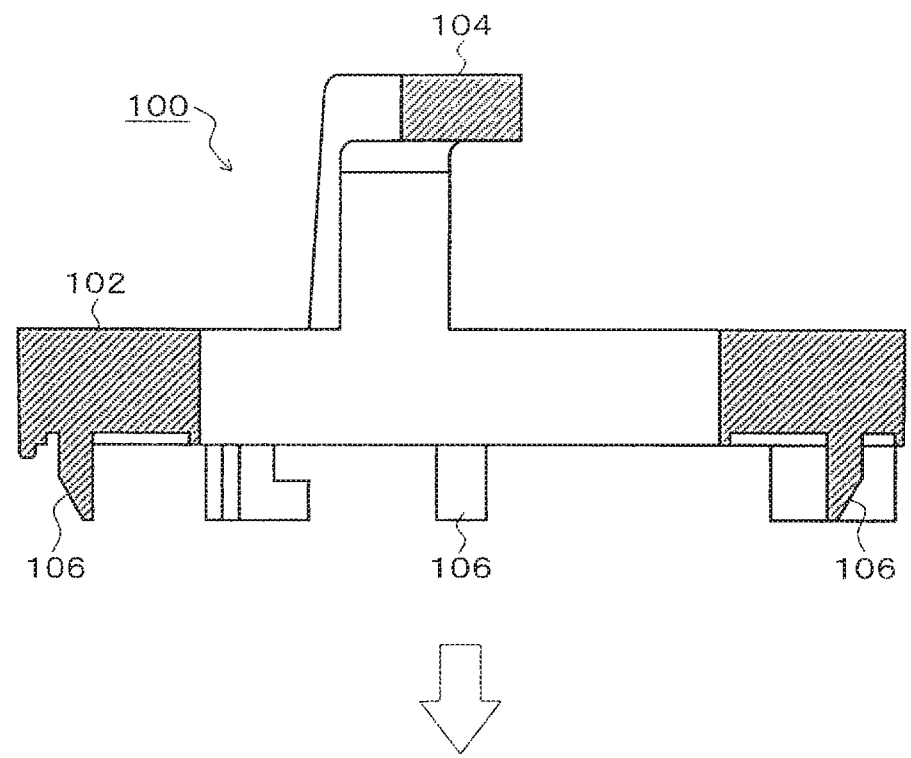
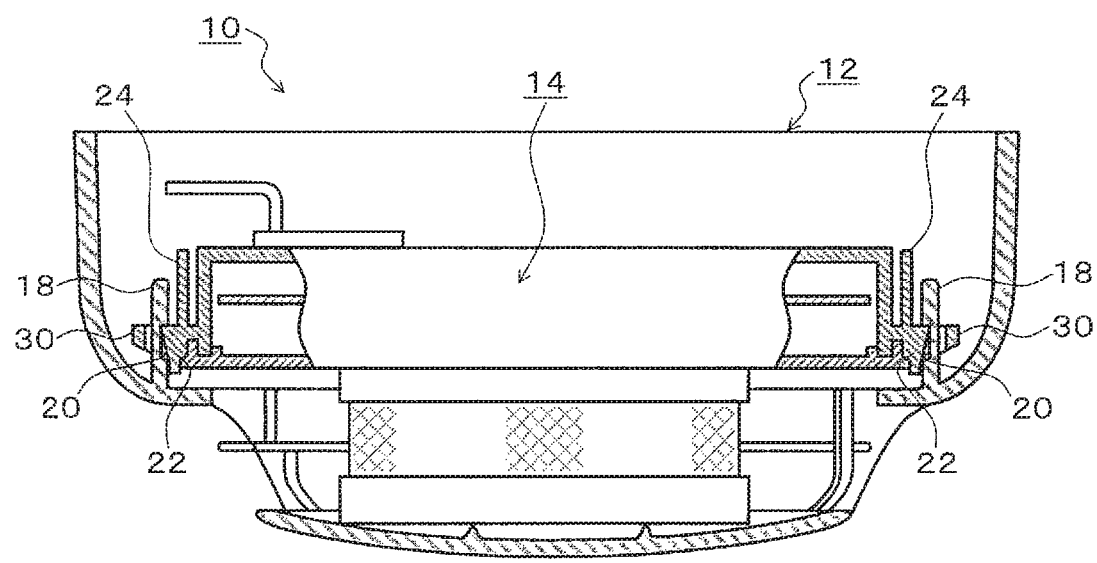

FIG. 13
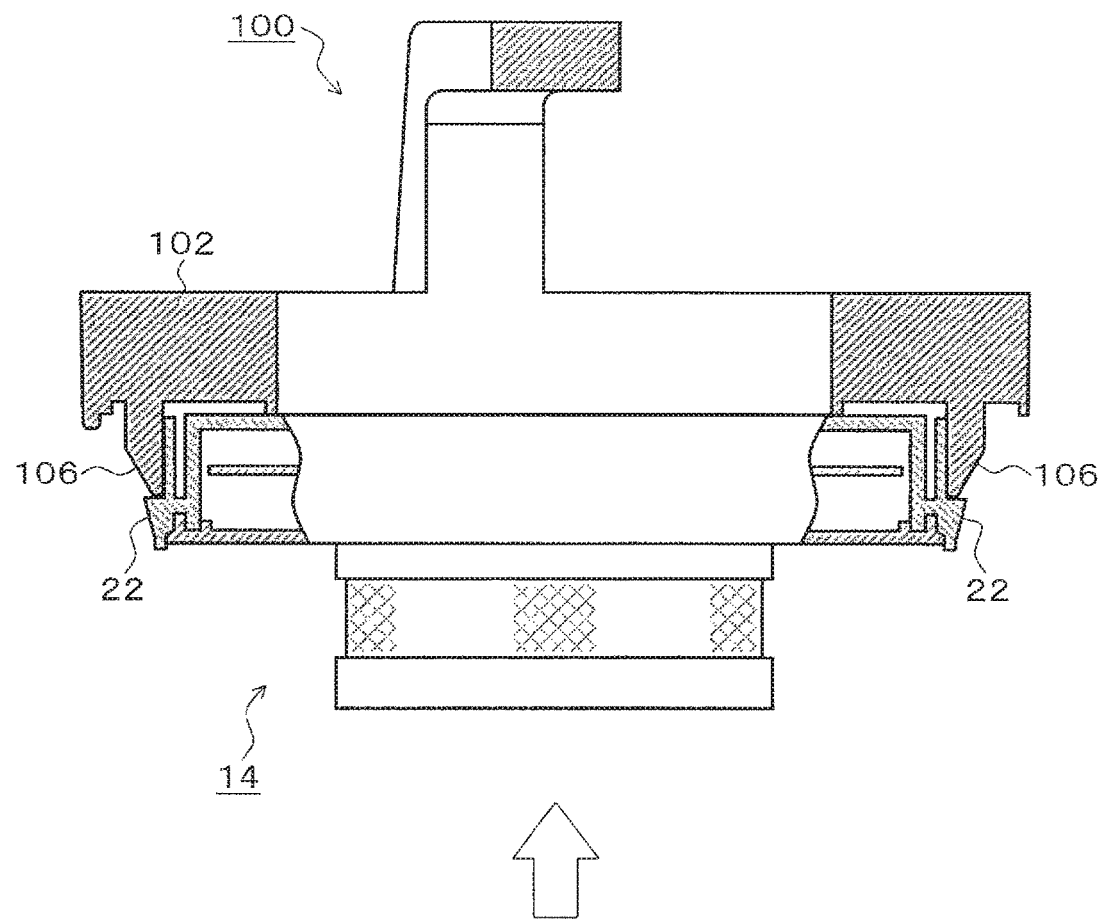
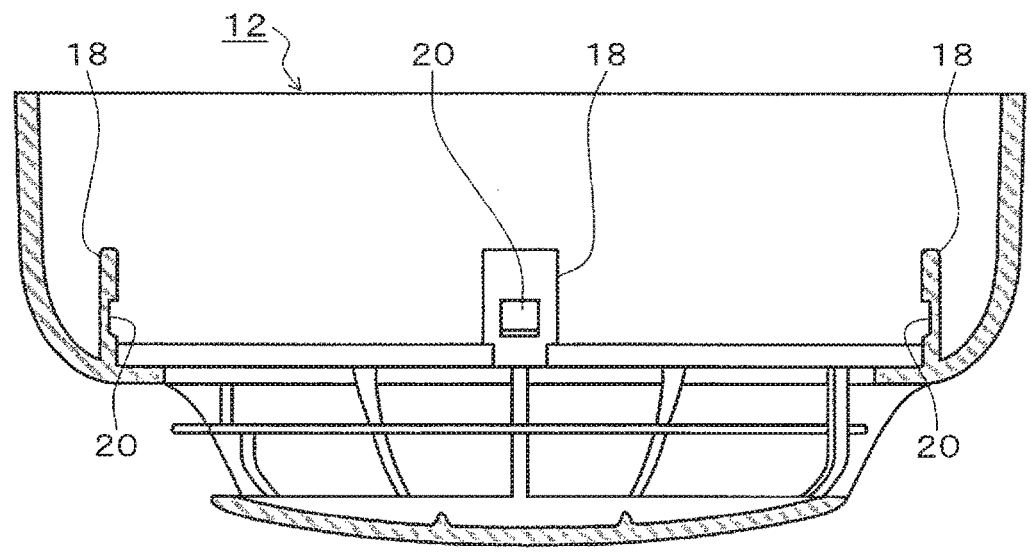

FIG. 14
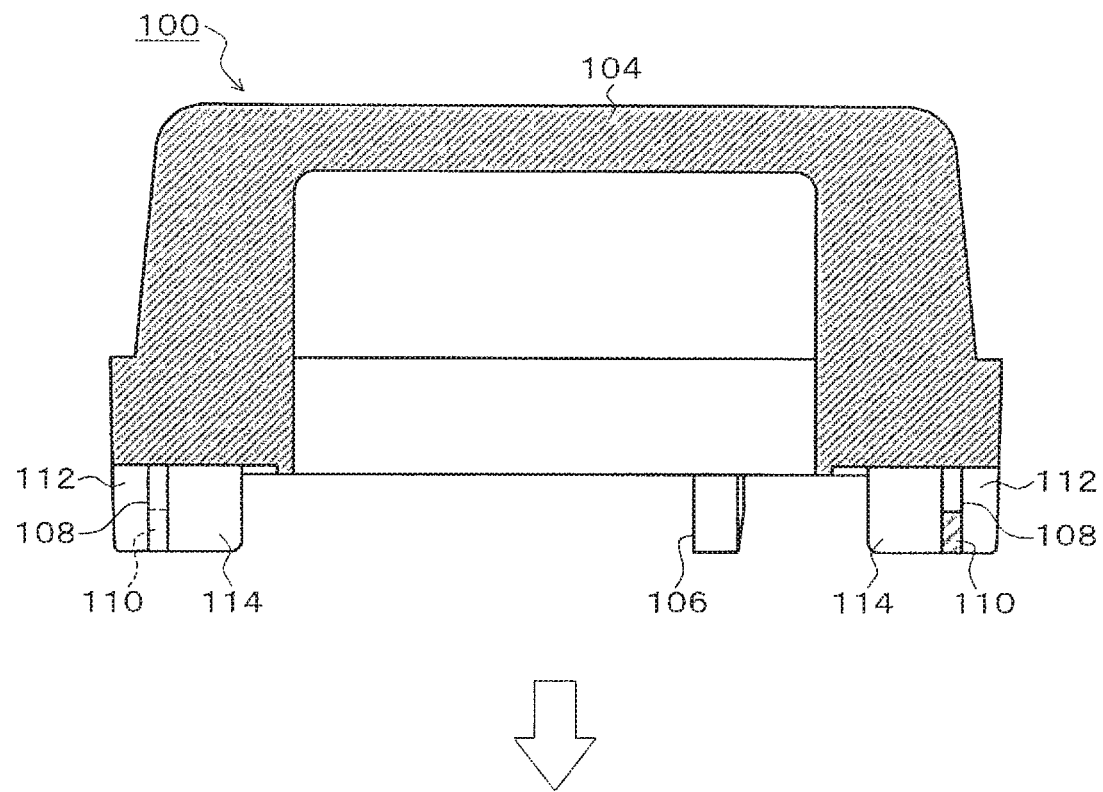
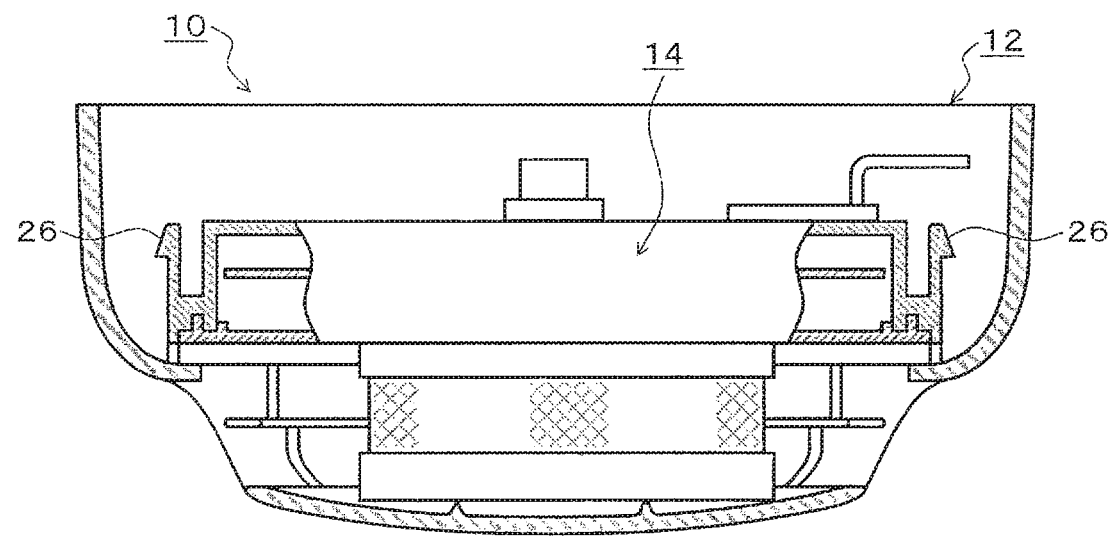

FIG. 17
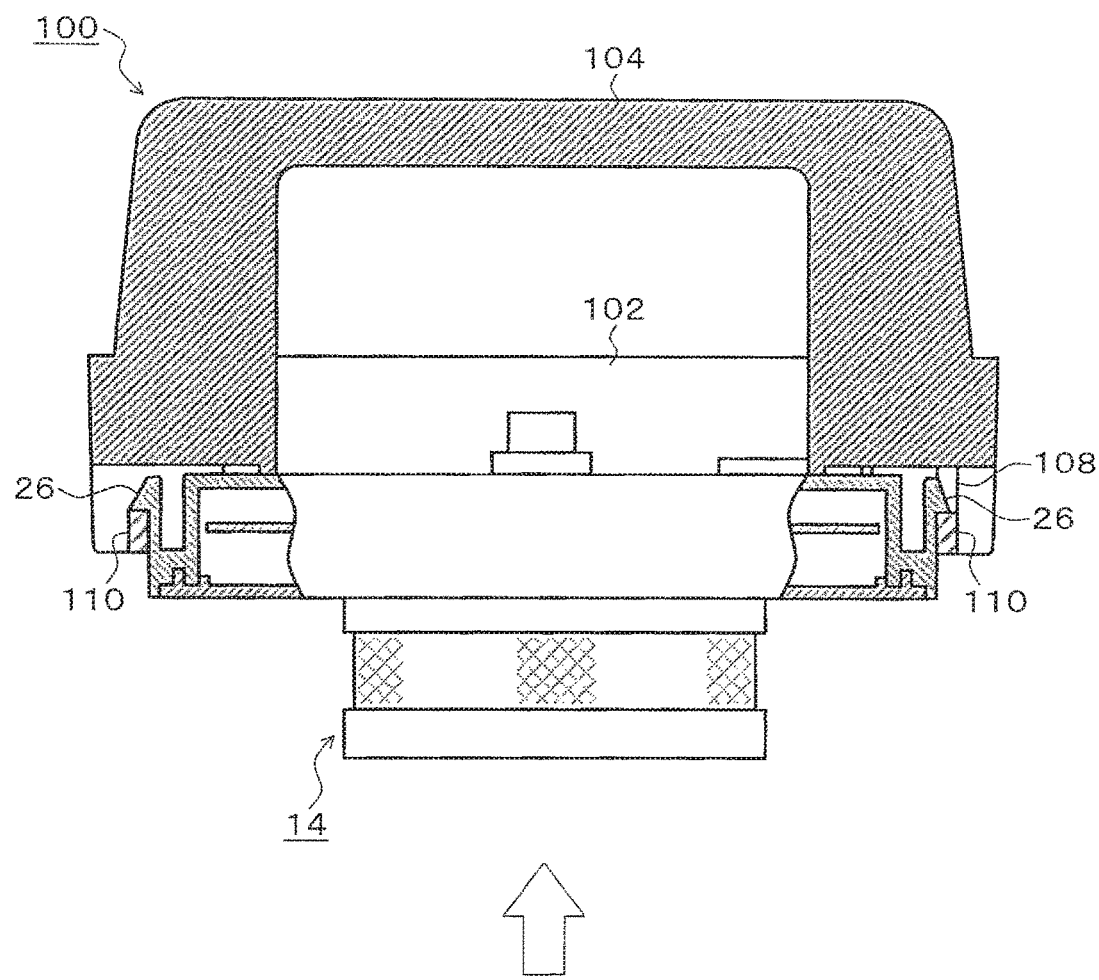
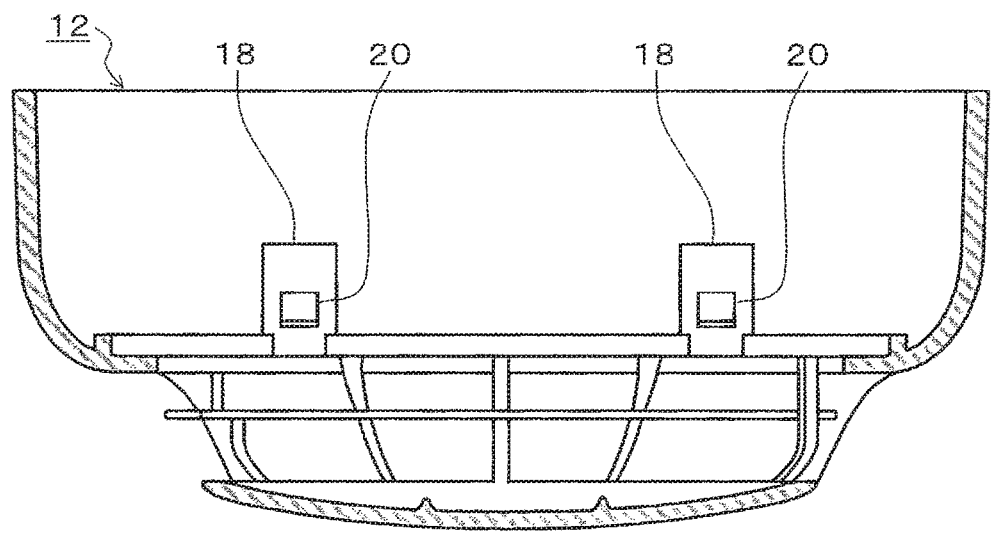

SENSOR SYSTEM, SENSOR, AND DETACHMENT TOOL

TECHNICAL FIELD

The present invention relates to a sensor, a detachment tool, and a sensor system having the sensor including a sensor cover and a sensor main body which is detachably disposed within the sensor cover, the sensor being disassembled using the detachment tool.

Priority is claimed on Japanese Patent Application No. 2012-093698 filed on Apr. 17, 2012, the contents of which are incorporated herein by reference.

BACKGROUND

In the related art, a sensor that transmits, when a fire is detected, a fire signal to a receiver and causes the receiver to output a fire alarm, is detachably attached to a sensor base disposed on a ceiling surface in a monitoring area. When the sensor is periodically inspected, there may be a case in which the sensor is detached from the sensor base and the detached sensor is disassembled to clean the inside.

In a sensor of the related art, for example, as described in Patent Document 1, a sensor main body is installed on the inside of a sensor cover, and when cleaning of the sensor is performed, a work of detaching the sensor main body from the sensor cover is performed.

In an attachment structure in which the sensor main body is installed on the inside of the sensor cover, for example, a fitting member is provided to stand on a plurality of positions on the outer circumference side of and the inside of the sensor cover, toward the opening of the cover. In the attachment structure, a fitting receiving member is provided on the sensor main body opposite the fitting member. The attachment structure is configured such that, when assembly in which the sensor main body is aligned to and inserted into the sensor cover is performed, the fitting member and the fitting receiving member are fitted and fixed to prevent detachment.

RELATED ART DOCUMENTS

Patent Documents

[Patent Document 1] Japanese Unexamined Patent Application, First Publication No. 2006-267128

SUMMARY OF INVENTION

Problems to be Solved by the Invention

However, in such sensor of the related art, disassembly is not taken into account. Therefore, when the sensor main body is detached from the sensor cover, a complicated detaching work in which a tool such as a driver is used and the fitting member at a plurality of positions is pushed and detached from the fitting receiving member is required, the detaching work requires effort and time, or there is a problem that the attachment structure may be damaged or broken.

Moreover, a dedicated detachment tool used to detach a sensor main body from a sensor cover is also proposed, but disassembly is not taken into account. Therefore, the detachment tool also has a complicated structure, the detachment tool becomes expensive and does not become common, or there is a problem that the detaching method requires a technique and even when the detachment tool is used, a specific technique is required for detaching work which is performed with alignment or rotation.

The present invention aims to provide a sensor system, a sensor, and a detachment tool enabling a sensor main body to be simply and easily detached from a sensor cover.

Means for Solving the Problem

In order to solve the aforementioned problem, an aspect of the present invention includes the following configurations.

(1) A first aspect of the present invention is a sensor system including: a sensor that is provided with a sensor cover having an opening formed on one end and a sensor main body which is detachably disposed on an inner portion of the sensor cover; and a detachment tool used to detach the sensor main body from the sensor cover, wherein the sensor includes an attachment structure used to attach the sensor main body to the inner portion of the sensor cover, the detachment tool includes a detachment structure used to detach the sensor main body from the inner portion of the sensor cover, and in the detachment structure, by pushing the detachment tool into the sensor main body from the opening of the sensor cover, the sensor main body is detached from the inner portion of the sensor cover.

(2) In the sensor system of the above (1), the attachment structure of the sensor may include: a fitting receiving member that is provided on the inner portion of the sensor cover and extends toward the opening of the sensor cover; and a fitting claw member that is provided on the sensor main body and fits the fitting receiving member when the sensor main body is inserted to an attachment position of the inner portion of the sensor cover, and the detachment structure of the detachment tool may include: a detachment claw member that is pushed into between the fitting receiving member and the fitting claw member and thereby releases a fitting state between the fitting receiving member and the fitting claw member.

(3) The sensor system of the above (1) may further include: a connection structure that detachably connects the detachment tool and the sensor main body when an attachment between the sensor cover and the sensor main body by the attachment structure of the sensor is released by the pushing of the detachment tool.

(4) In the sensor system of the above (3), the connection structure may include: a connection claw member provided on the sensor main body; and a connection receiving member provided on the detachment tool, and wherein the connection claw member may be fitted and connected to the connection receiving member when the detachment tool is pushed into the sensor main body, and a connection state between the connection claw member and the connection receiving member may be released by rotating the detachment tool relative to the sensor main body.

(5) In the sensor system of the above (4), the connection receiving member of the detachment tool may include a connection receiving section of a cantilever structure extending to have a tip portion in an inverse L shape or an L shape, the connection claw member may be fitted and connected to the connection receiving section when the detachment tool is pushed into the sensor main body, and a connection state between the connection claw member and the connection receiving member may be released by rotating the detachment tool relative to the sensor main body.

(6) A second aspect of the present invention is a sensor including: a sensor cover having an opening formed on one end; a sensor main body disposed on an inner portion of the sensor cover; and an attachment structure used to detachably attach the sensor main body to the inner portion of the sensor cover, wherein by pushing a detachment tool from the opening of the sensor cover into the sensor main body disposed on the inner portion, an attachment by the attachment structure is released.

(7) In the sensor of the above (6), the attachment structure of the sensor may include: a fitting receiving member that is provided on the inner portion of the sensor cover and extends toward the opening of the sensor cover; and a fitting claw member that is provided on the sensor main body and fits the fitting receiving member when the sensor main body is inserted to an attachment position of the inner portion of the sensor cover.

(8) The sensor of the above (6) may include: a connection structure that detachably connects the detachment tool and the sensor main body when the detachment tool is pushed and an attachment between the sensor cover and the sensor main body by the attachment structure is released.

(9) A third aspect of the present invention is a detachment tool used to detach a sensor including: a sensor cover having an opening formed on one end; a sensor main body disposed on an inner portion of the sensor cover; and an attachment structure used to detachably attach the sensor main body to the inner portion of the sensor cover, from the sensor cover by releasing an attachment by the attachment structure, the detachment tool including: a detachment claw member that is pushed into the sensor main body from the opening of the sensor cover and thereby the attachment by the attachment structure of the sensor is released to detach the sensor main body from the sensor cover.

(10) The detachment tool of the above (9) may include: a connection structure that detachably connects the detachment tool and the sensor main body when the sensor main body is detached from the sensor cover by the detachment claw member.

(11) In the detachment tool of the above (10), the connection structure may include a connection receiving member, a connection claw member provided on the sensor main body may be fitted and connected to the connection receiving member when the detachment tool is pushed into the sensor main body, and a connection state between the connection claw member and the connection receiving member may be released by rotating the detachment tool relative to the sensor main body.

(12) In the detachment tool of the above (11), the connection receiving member of the detachment tool may include a connection receiving section of a cantilever structure extending to have a tip portion in an inverse L shape or an L shape, the connection claw member of the sensor main body may be fitted and connected to the connection receiving section when the detachment tool is pushed into the sensor main body, and a connection state between the connection claw member and the connection receiving member may be released by rotating the detachment tool relative to the sensor main body.

Advantage of the Invention

According to the sensor system and the sensor of the above (1) to (8), with respect to the sensor including the attachment structure in consideration of disassembly in which the sensor main body is detachably attached to the inside of the sensor cover, it is possible to disassemble the sensor and to simply and easily detach the sensor main body from the sensor cover by a so-called one-touch operation to push the detachment tool from the opening of the sensor cover into the sensor main body which is installed on the inside and is fixed. In addition, it is possible to improve work efficiency of an operation to disassemble the sensor for cleaning performed with a periodic inspection or the like, and to reliably avoid damage or breakage of the sensor accompanied by the disassembly operation.

Moreover, when the sensor is disassembled by the one-touch operation of the detachment tool and the sensor main body is detached from the sensor cover, the sensor main body is connected to the detachment tool, and it is possible to easily take out the sensor main body from the sensor cover in a state where the sensor main body is connected to the detachment tool. Furthermore, by relatively rotating the sensor main body connected to the detachment tool in a direction to release the connection, it is possible to easily detach the sensor main body from the detachment tool.

According to the detachment tool of the above (9) to (12), since the detachment structure is simple, mass production by metallic molding is available, and it is possible to provide a low-cost tool.

BRIEF DESCRIPTION OF THE DRAWINGS

FIG. 11 is a view showing a situation in which the detachment tool is pushed into the sensor.

FIG. 13 is a view showing a state where the sensor main body is taken out from the sensor cover by the detachment tool.

FIG. 14 is a view showing the situation in which the detachment tool is pushed into the sensor with respect to a connection position with the sensor main body.

FIG. 17 is a view showing a state where the sensor main body connected to the detachment tool is taken out from the sensor cover.

DESCRIPTION OF THE EMBODIMENTS

[Overview of Sensor System]

A sensor system of the present invention includes a sensor (fire sensor) having an attachment structure in consideration of disassembly (for easy disassembly) in which a sensor main body is detachably attached to an inner portion of a sensor cover, and a detachment tool used to detach the sensor main body from the sensor cover of the sensor. Hereinafter, embodiments of the sensor, the detachment tool, and a detachment operation will be described in order.

[Configuration of Sensor]

Figure 1:
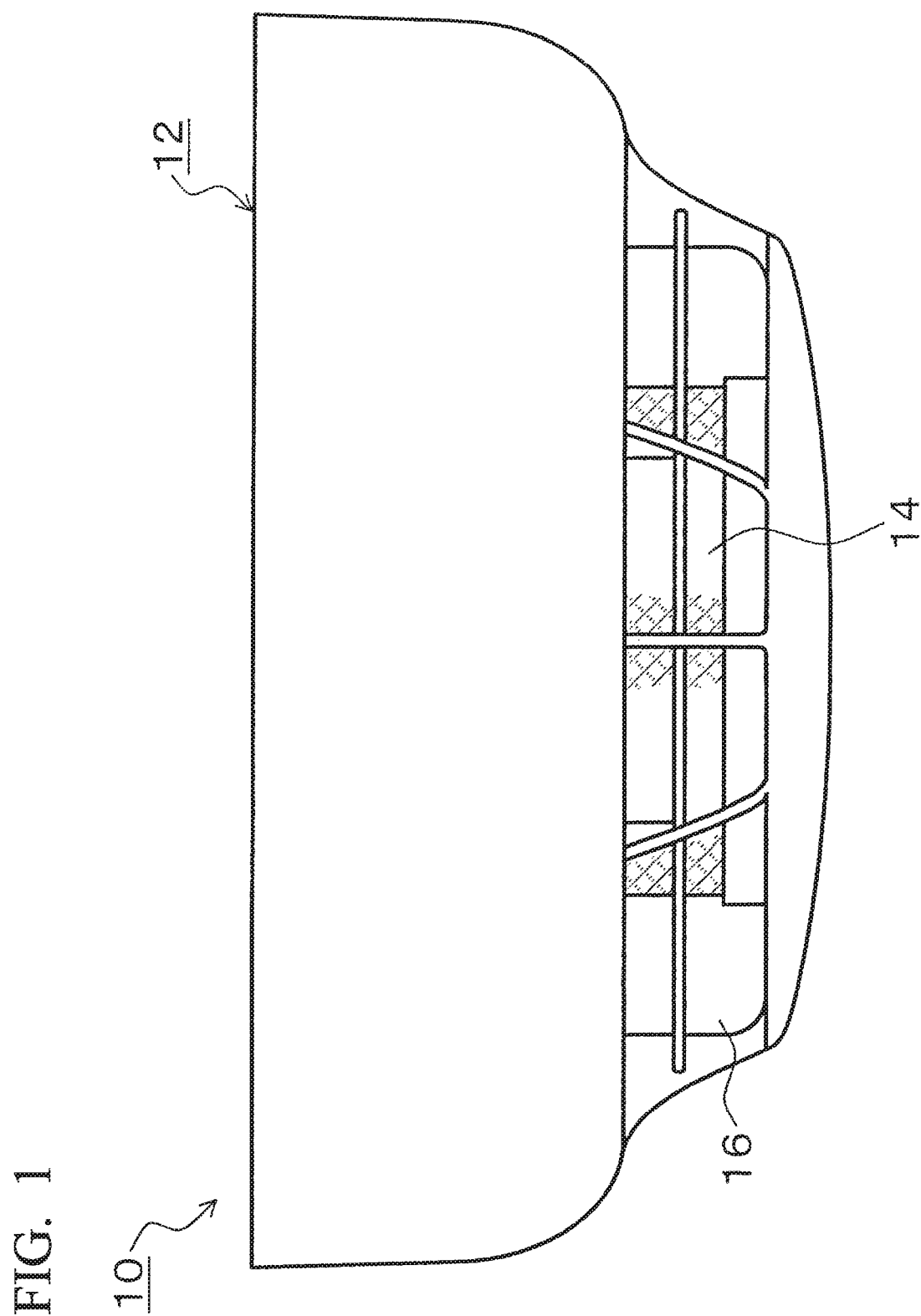
FIG. 1 is an external view of a sensor of the present invention.

As shown in FIG. 1, a sensor 10 targeted by the present invention is configured by a sensor cover 12 and a sensor main body 14, and the sensor main body 14 is detachably attached to an inner portion of the sensor cover 12 in consideration of disassembly.

The sensor cover 12 is a storage body in a bowl shape having an opening on the upper side of the drawing, has a smoke flow inlet 16 formed in the outer circumference in a downward part of the drawing, and is configured to introduce smoke accompanied by a fire into a smoke detection section of the sensor main body 14 disposed on the inside. In addition, the sensor cover 12 and the sensor main body 14 are synthetic resin members formed by metallic molding and/or an assembled body of the members.

Figure 2:
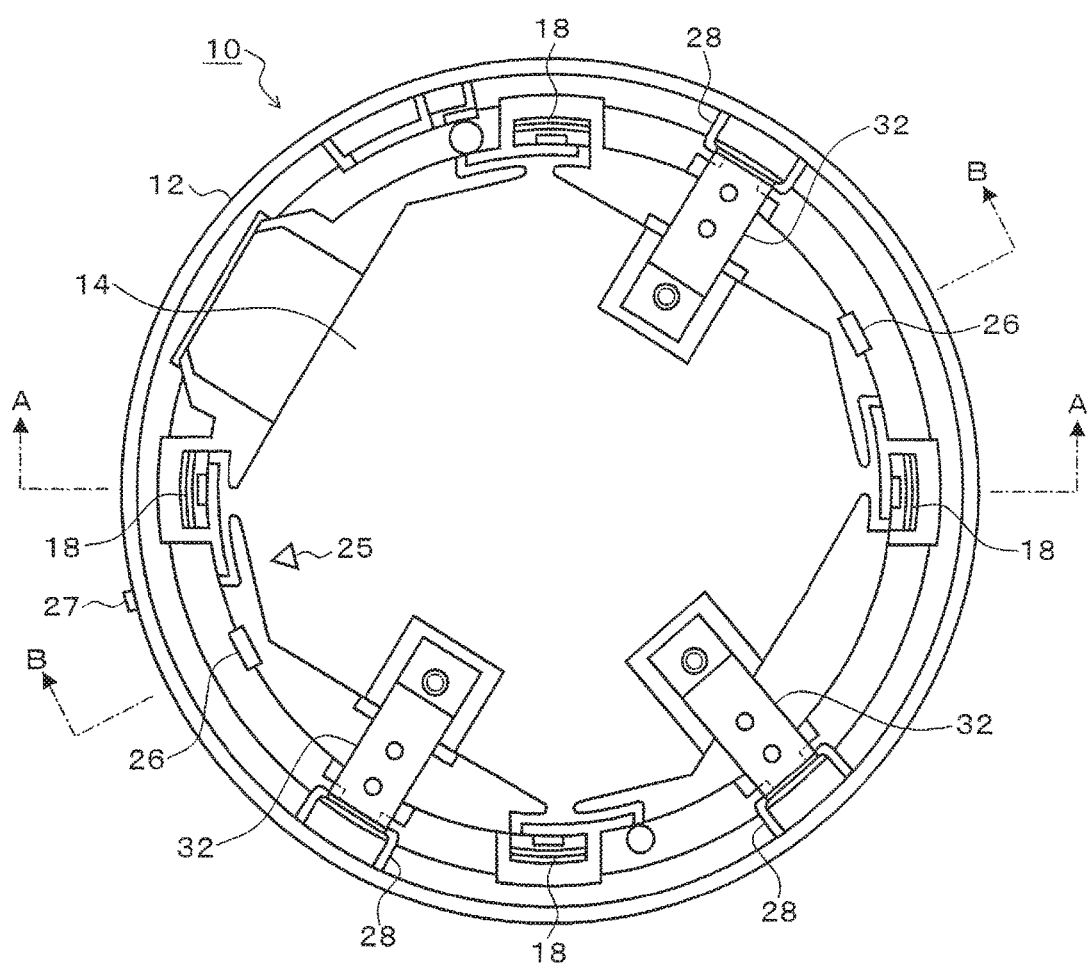
FIG. 2 is a plan view of the sensor of FIG. 1.

FIG. 2 is a plan view looking from the upside of the drawing at the sensor 10 of FIG. 1. The sensor main body 14 is attached and fixed in a state where the sensor main body 14 is installed on the inside from the opening of the sensor cover 12. In the sensor main body 14, a terminal metal part 32 bent in an L shape is disposed on three places, and by the terminal metal part 32, the sensor main body 14 can be connected electrically and mechanically to a sensor base (not shown in the drawing) by pushing the sensor main body 14 toward a sensor base fixed to a ceiling surface in a monitor region and rotating the sensor main body 14.

Figure 3:
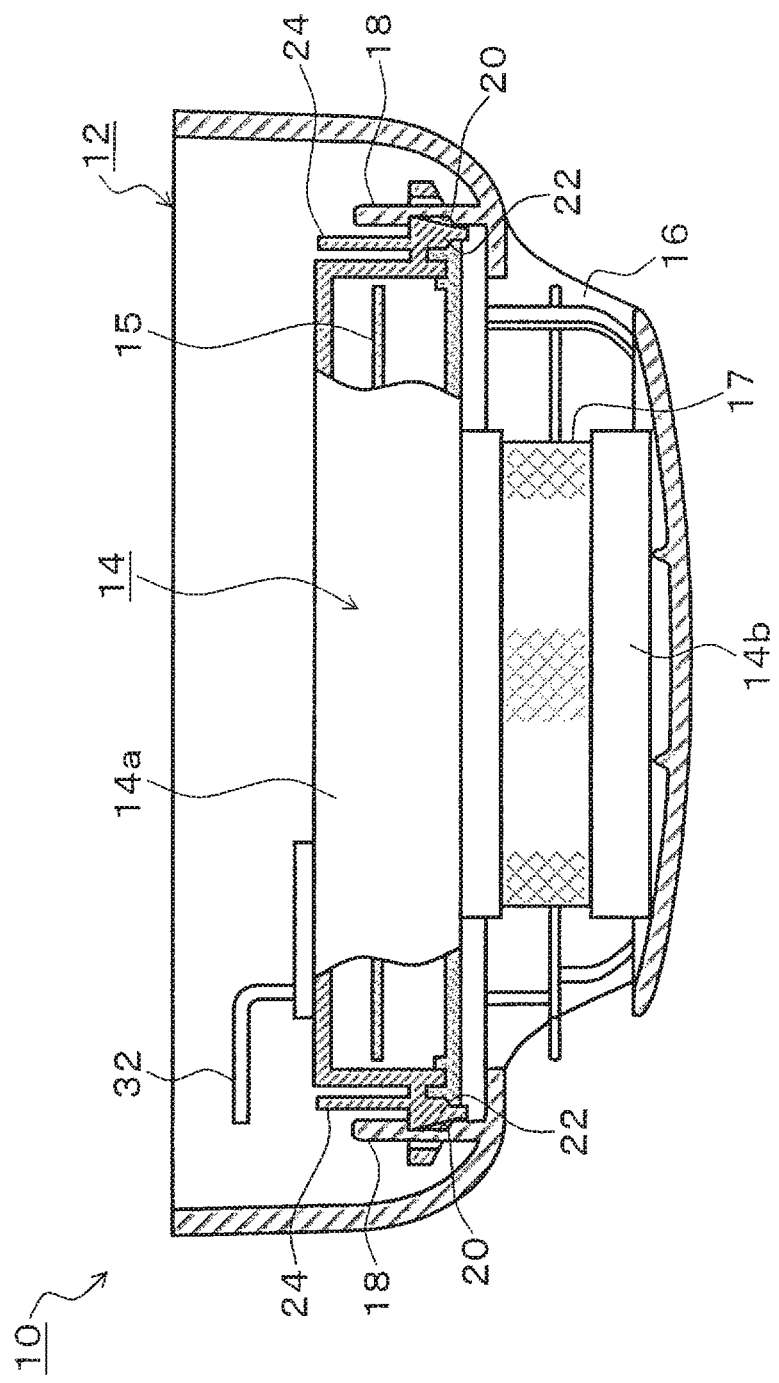
FIG. 3 is an inside structure view by a vertical cross section along an A-A line of FIG. 2.

FIG. 3 is a view showing an inside structure by a vertical cross section along an A-A line of FIG. 2. The sensor cover 12 is opened upwardly of the drawing and has a bowl shape as a whole. The sensor cover 12 has a step section formed to narrow the lower portion in the center and has the smoke flow inlet 16 which introduces smoke, formed in the outer circumference of the lower portion.

A fitting receiving member 18 is provided to stand toward the opening in the upward part of the drawing on the inside of the step section of the sensor cover 12. The fitting receiving member 18 has a fitting concave section 20 formed on the inside.

The sensor main body 14 is configured by a circuit storage section 14a having a large diameter on the upside of the drawing and a smoke detection section 14b having a small diameter on the downside of the drawing. The circuit storage section 14a stores a circuit substrate 15 on which a sensor circuit is mounted. A known scattered-light smoke detection structure, for example, a structure disclosed in Patent Document 1 is provided on the smoke detection section 14b of the sensor main body 14.

The scattered-light smoke detection structure has a smoke detection room formed on the inside, has a light emitting section and a light receiving section provided on the smoke detection room. The scattered-light smoke detection structure receives, by the light receiving section, scattered light occurring when light from the light emitting section is incident on smoke which flows into the smoke detection room from the smoke flow inlet 16, converts the received light into an electric signal to output a light receiving signal, and detects a fire based on the light receiving signal. In addition, an insect net 17 is provided in the outer circumference of the smoke detection section 14b, and a labyrinth structure (not shown in the drawing) that passes smoke but cuts off light from the outside is provided on the inside of the insect net 17.

On the outer circumference side of the circuit storage section 14a of the sensor main body 14, a fitting claw member 22 is formed to protrude in a lateral direction of the drawing, and a guide rib 24 stands on the inside of the fitting claw member 22.

As shown in FIG. 2, the fitting receiving member 18 is provided on four places in a circumferential direction within the sensor cover 12. Correspondingly, the fitting claw member 22 of the sensor main body 14 is also provided on four places in the outer circumference of the circuit storage section 14a.

When the sensor main body 14 is installed within the sensor cover 12, the fitting claw member 22 provided on the sensor main body 14 is fitted to the fitting concave section 20 of the fitting receiving member 18 provided to stand on the inside of the sensor cover 12 and is fixed to prevent detachment.

In this way, the attachment structure in consideration of disassembly in which the sensor main body 14 is detachably attached to the inside of the sensor cover 12 of the sensor 10 of the present invention is configured by the fitting receiving member 18 provided within the sensor cover 12 to stand toward the opening of the cover and having the fitting concave section 20 formed thereon, and the fitting claw member 22 provided on the sensor main body 14 so as to fit the fitting concave section 20 of the fitting receiving member 18.

Figure 4:
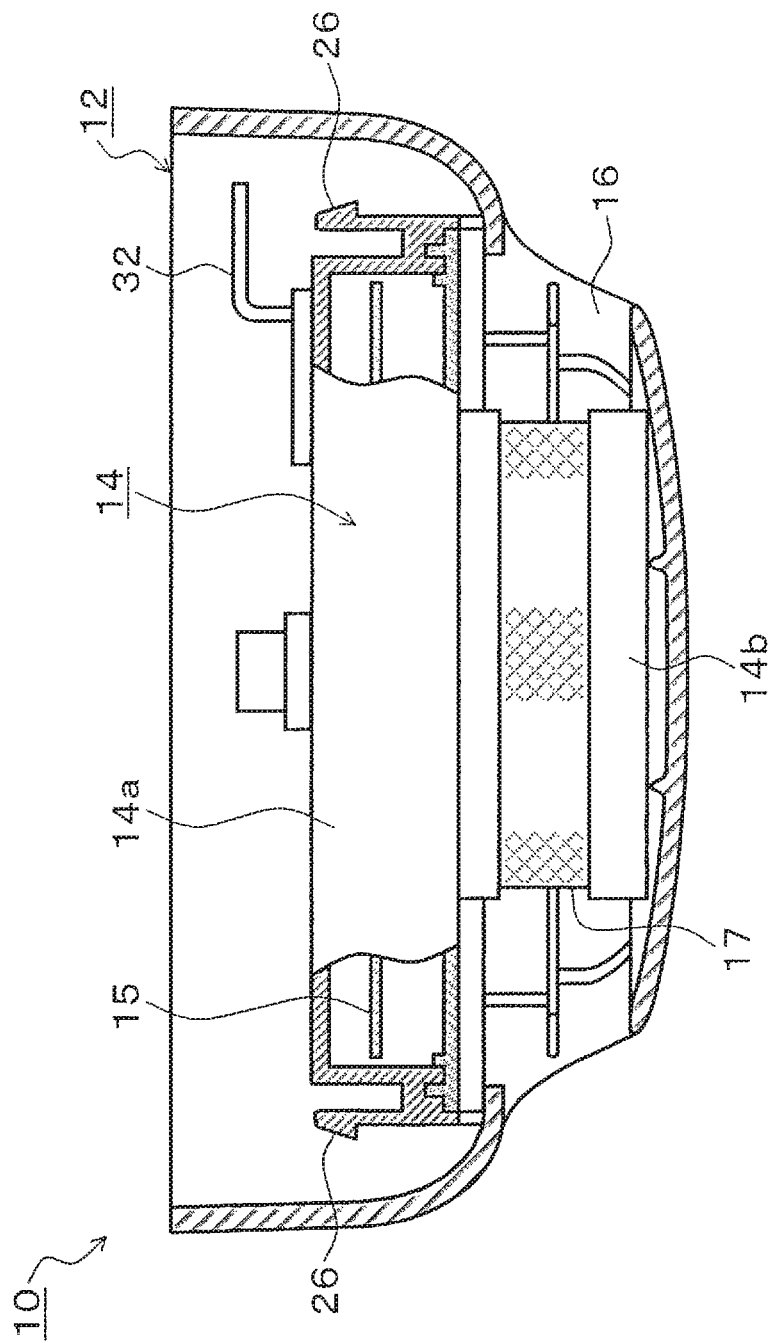
FIG. 4 is an inside structure view by a vertical cross section along a B-B line of FIG. 2.

FIG. 4 is a view showing a vertical cross section along a B-B line of FIG. 2. On the outer circumference of the circuit storage section 14a in the sensor main body 14, a connection claw member 26 is provided to stand toward the opening in the upward part of the drawing. The connection claw member 26 configures a connection structure of the sensor main body 14 side so as to connect the sensor main body 14 to a detachment tool 100 described below. As shown in FIG. 2, the connection claw member 26 is provided on two places opposing each other on the outer circumference side of the sensor main body 14.

Figure 5:
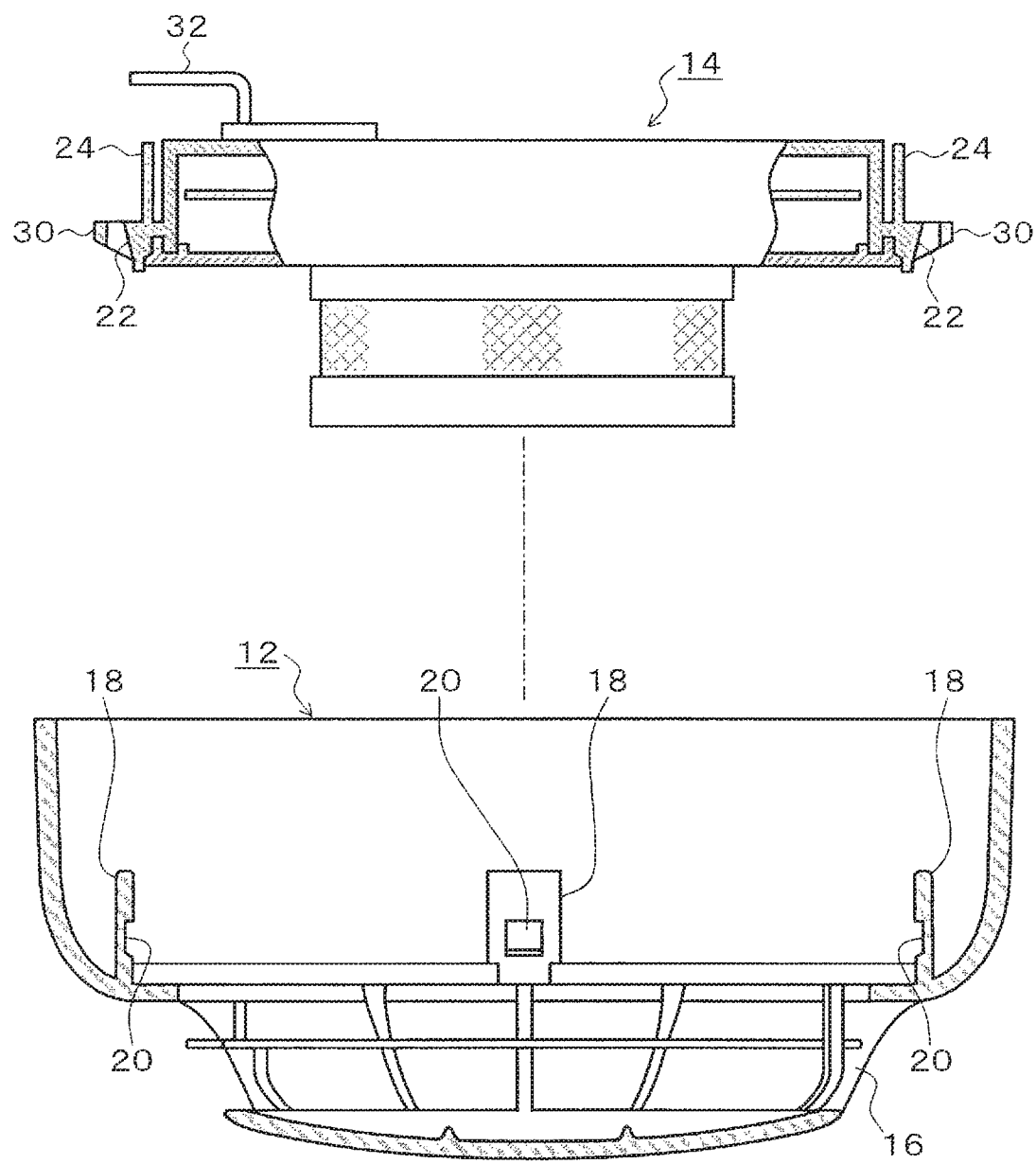
FIG. 5 is a view showing a disassembled sensor cover and sensor main body.

FIG. 5 is an exploded view of the sensor cover 12 and sensor main body 14 shown in the same cross section as that of FIG. 3. When the sensor main body 14 is installed in the sensor cover 12, by positioning the fitting claw member 22 of the sensor main body 14 so as to oppose the fitting receiving member 18 provided to stand within the sensor cover 12 and in this state, installing the sensor main body 14 in the sensor cover 12, the sensor main body 14 can be fixed to prevent detachment within the sensor cover 12 as shown in FIG. 3. The installation work in this case can be made with a simple operation in which the sensor main body 14 is aligned to and fitted into the sensor cover 12.

Figure 6:
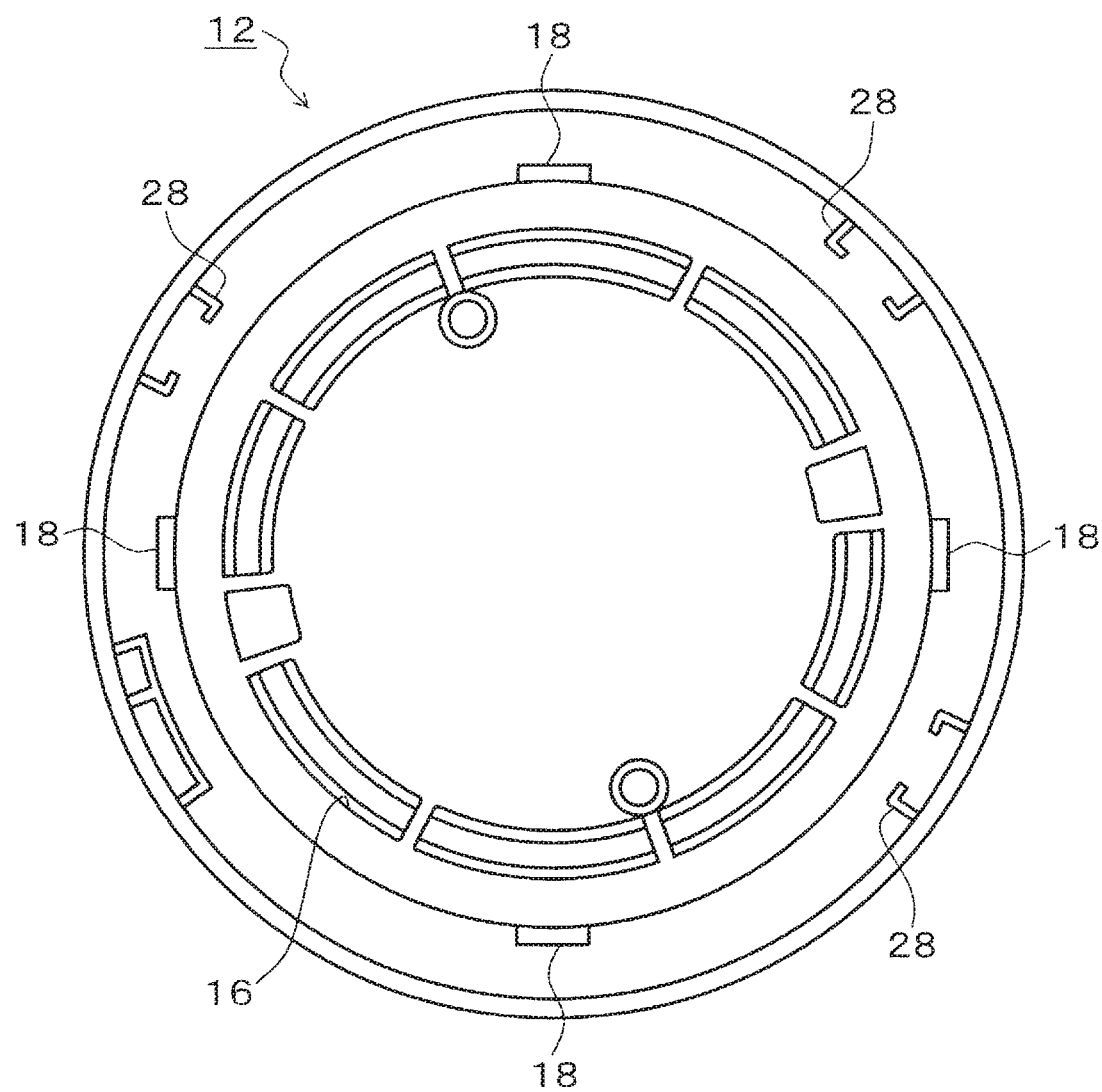
FIG. 6 is a plan view looking at the inside of the sensor cover from an opening.

FIG. 6 is a plan view showing the sensor cover 12 looking from the opening side. The fitting receiving member 18 is provided to stand separately in four places on the inside of the step section. In addition, a positioning groove 28 is provided separately in three places on the inside of the opening of the sensor cover 12. By fitting a positioning rib 34 (refer to FIG. 7) provided on the sensor main body 14 into the positioning groove 28, an attachment position of the sensor main body 14 relative to the sensor cover 12 is unambiguously determined.

Figure 7:
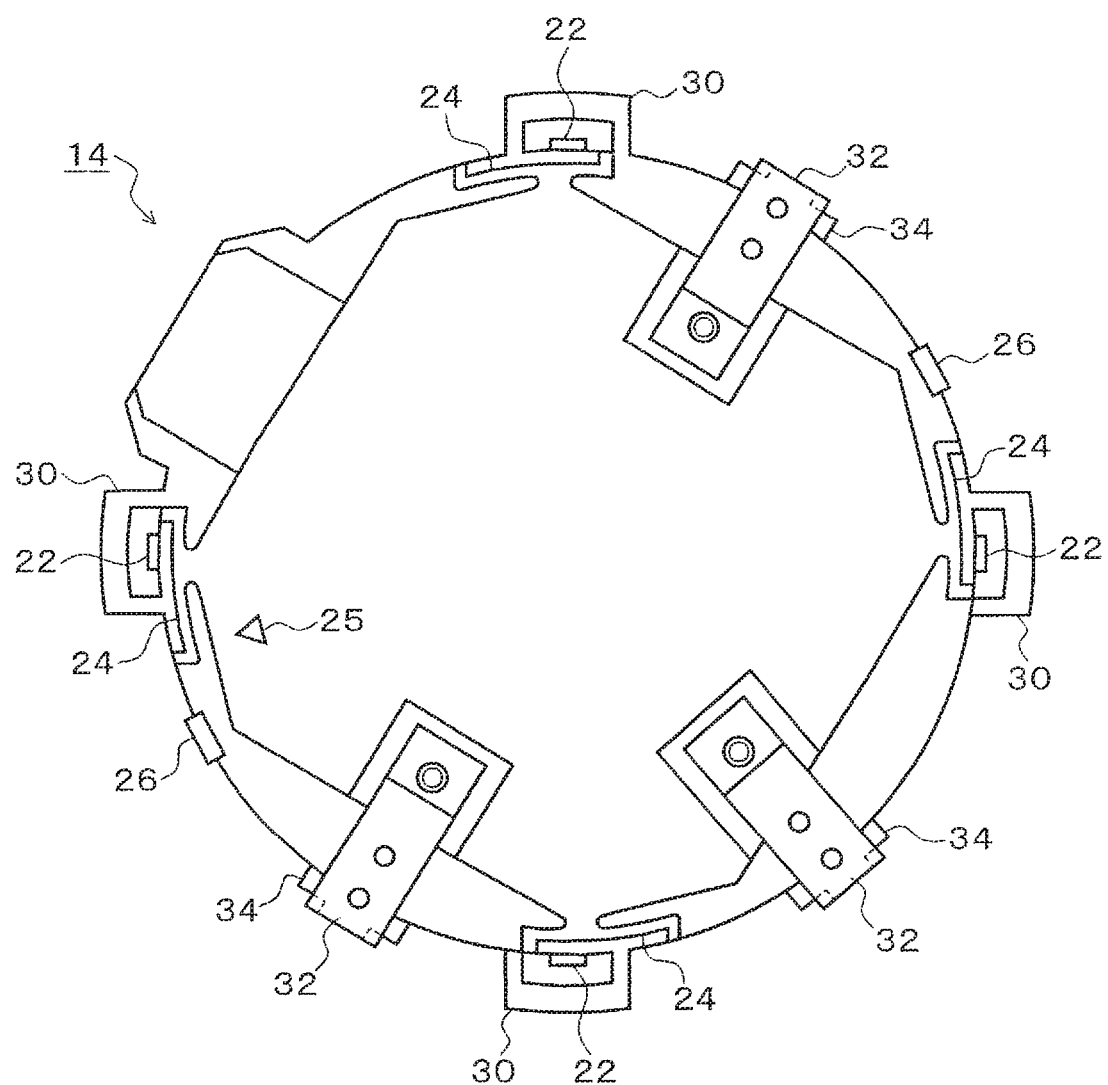
FIG. 7 is a plan view of the sensor main body.

FIG. 7 is a plan view showing the sensor cover 14 looking from the opening side as in the case of the sensor cover 12 of FIG. 6. The fitting claw member 22 is provided to protrude in four separate places on the outer circumference of the sensor main body 14. The fitting claw member 22 is configured such that a guide frame 30 is provided surrounding the fitting claw member 22 and by installing the fitting receiving member 18 of the sensor cover 12 shown in FIG. 6 so as to be inserted into the guide frame 30, the fitting claw member 22 is fitted to the fitting concave section 20 (refer to FIG. 3) of the fitting receiving member 18. In addition, the guide rib 24 is provided to stand on the inside of the fitting claw member 22, and a detachment claw member 106 (refer to FIG. 9) provided on the detachment tool 100 described below is guided to a fitting part between the fitting claw member 22 and the fitting receiving member 18.

[Configuration of Detachment Tool]

A detachment tool according to the present invention includes a detachment structure used to release (disassemble) the attachment by the attachment structure of the sensor 10 shown in FIG. 1 to FIG. 7 and detach the sensor main body 14 from the sensor cover 12.

Figure 8:
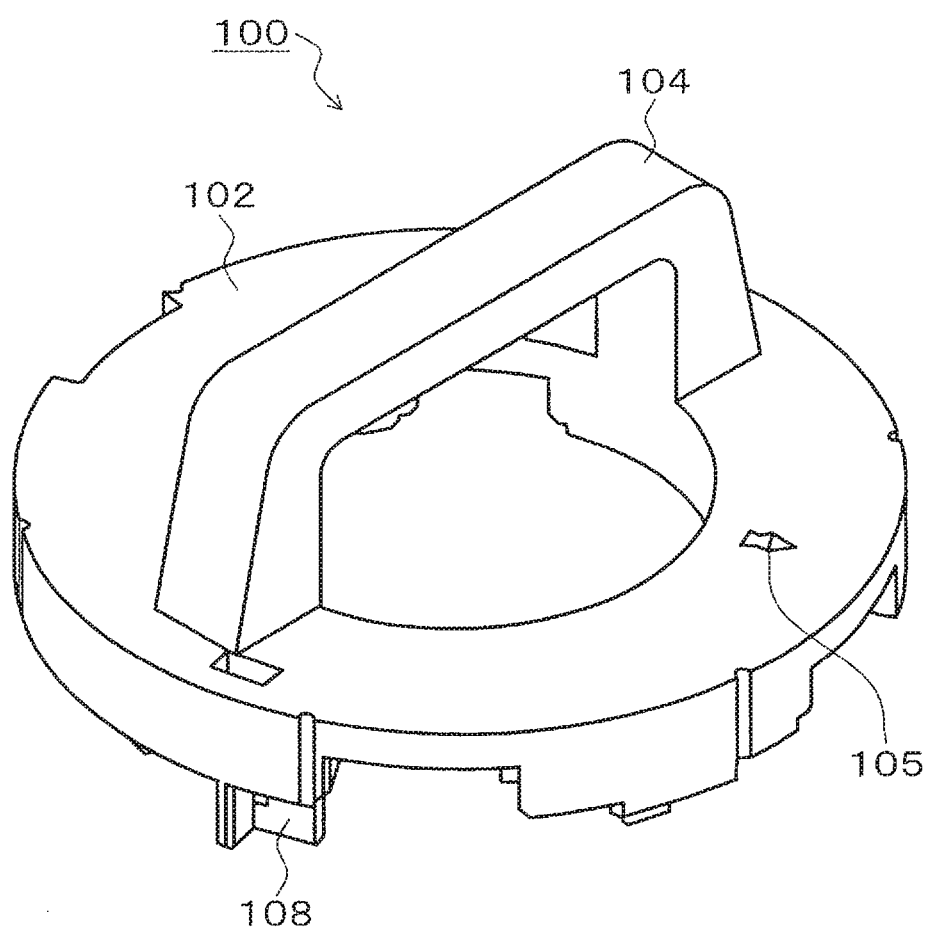
FIG. 8 is an external view of a detachment tool used in the present invention.

FIG. 8 is a view showing the appearance of the detachment tool 100 used in the present invention. In FIG. 8, the detachment tool 100 is provided with a handle 104 on the upside of a ring-shaped tool main body 102 and is provided with the detachment structure described below on the downside of the tool main body 102. In addition, a marker 105 is provided on the top surface of the tool main body 102, and positioning of the detachment tool 100 to the sensor 10 can be made by aligning the marker 105 to a marker 25 provided on the top surface of the sensor main body 14 shown in FIG. 2. Note that, positioning of the detachment tool 100 to the sensor 10 can be also made by aligning the marker 105 of the tool main body 102 to a base positioning rib 27 provided on the outer circumference of the sensor cover 12 other than the marker 25 of the sensor main body 14.

Figure 9:
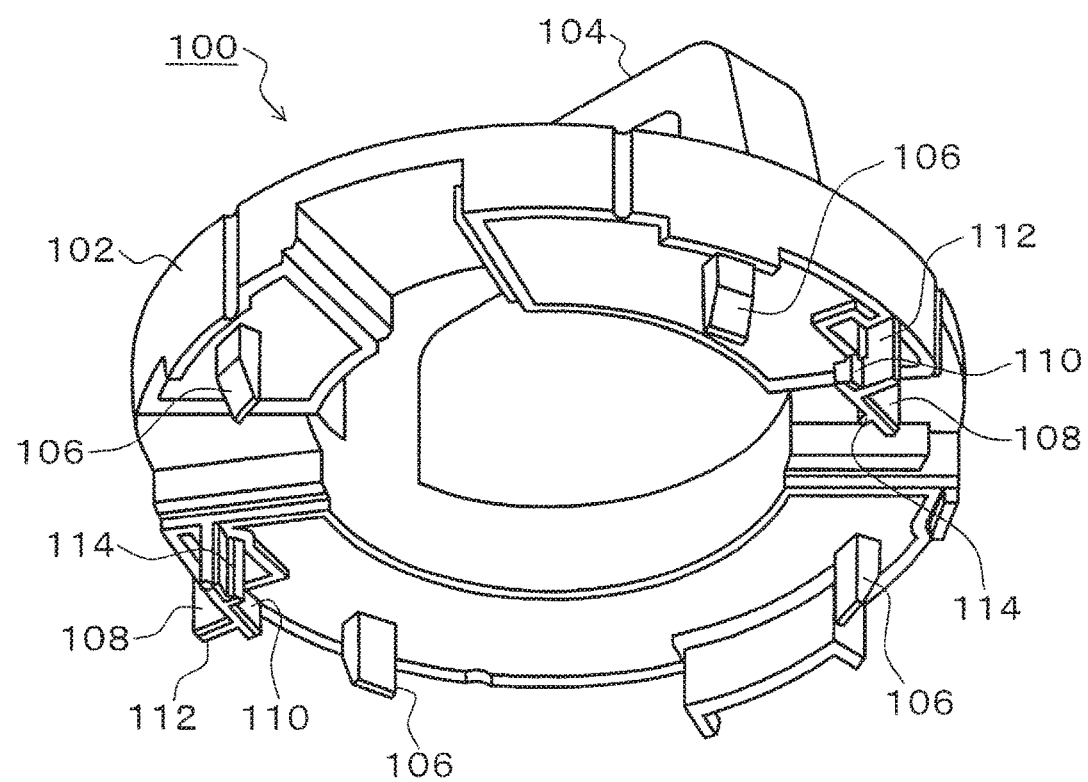
FIG. 9 is a view looking at the detachment tool of FIG. 8 from a lower side.

FIG. 9 is a view looking at the detachment tool 100 from the lower side. As a detachment structure of the tool side, a detachment claw member 106 is provided to stand in a downward direction of the drawing separately in four places on the downside of the tool main body 102. The detachment claw member 106 is in a wedge form having a taper surface on the outer side.

In addition, as a connection structure of the tool side so as to hold the sensor main body 14 detached from the sensor cover 12, a connection receiving member 108 is provided to stand separately in two places opposing each other on the downside of the tool main body 102. The connection receiving member 108 is in a cantilever form having a tip portion in an inverse L shape looking from the outer side, and the tip portion of the cantilever form is a connection receiving section 110.

In addition, an outward guide rib 112 that projects outwardly and an inward guide rib 114 that projects inwardly are integrally formed on the connection receiving member 108. The outward guide rib 112 is configured such that positioning to an inner wall of the sensor cover 12 that is positioned outwardly can be performed. The inward guide rib 114 is configured such that positioning to an outer wall of the sensor main body 14 that is positioned inwardly can be performed.

Figure 10:
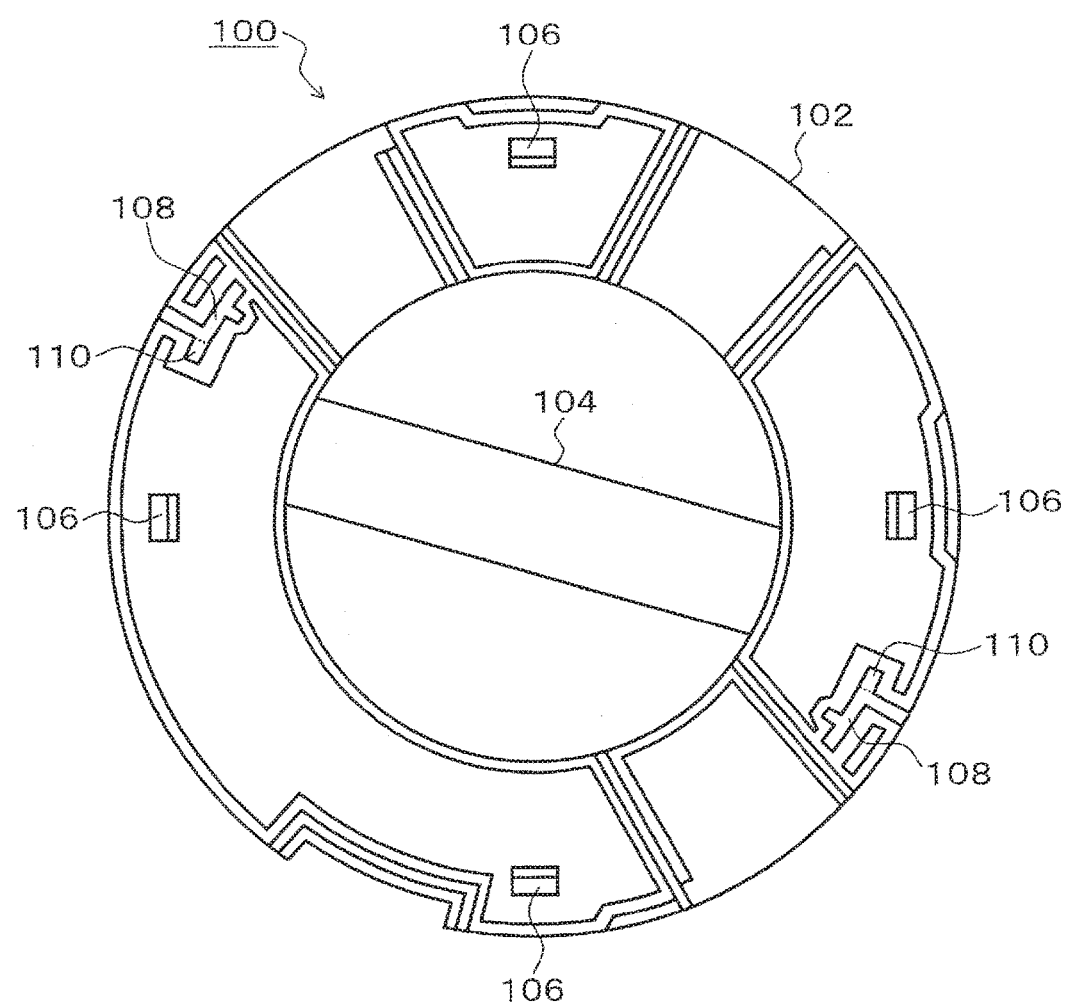
FIG. 10 is a plan view looking at the detachment tool of FIG. 8 from a lower side.

FIG. 10 is a plan view showing the tool main body 102 of the detachment tool 100 looking from the lower side. The detachment claw member 106 is provided separately in four places, and the connection receiving member 108 including the connection receiving section 110 is provided separately in two places.

The detachment tool 100 having the structure shown in FIG. 8 to FIG. 10 can be produced by metallic molding using synthetic resin materials. Since mass production is available, it is possible to provide the detachment tool at a low cost.

[Detachment Operation of Sensor Main Body Using Detachment Tool]

In the present invention, by using the detachment tool 100 shown in FIG. 8 to FIG. 10, it is possible to disassemble the sensor 10 shown in FIG. 1 to FIG. 4 and to detach the sensor main body 14 from the sensor cover 12 by a one-touch operation.

(Fitting Release of Attachment Structure)

FIG. 11 is a view showing a situation in which the detachment tool 100 is pushed into the sensor 10. When positioning is performed such that the marker 105 (refer to FIG. 8) of the detachment tool 100 is aligned to the marker 25 (refer to FIG. 2) of the sensor main body 14 installed in the sensor 10, as shown in FIG. 11, the detachment claw member 106 of the detachment tool 100 opposes the fitting receiving member 18 of the sensor cover 12 which is a fitting structure between the sensor cover 12 and the sensor main body 14 in the sensor 10. In this state, the detachment tool 100 is pushed into the sensor cover 12.

Figure 12:
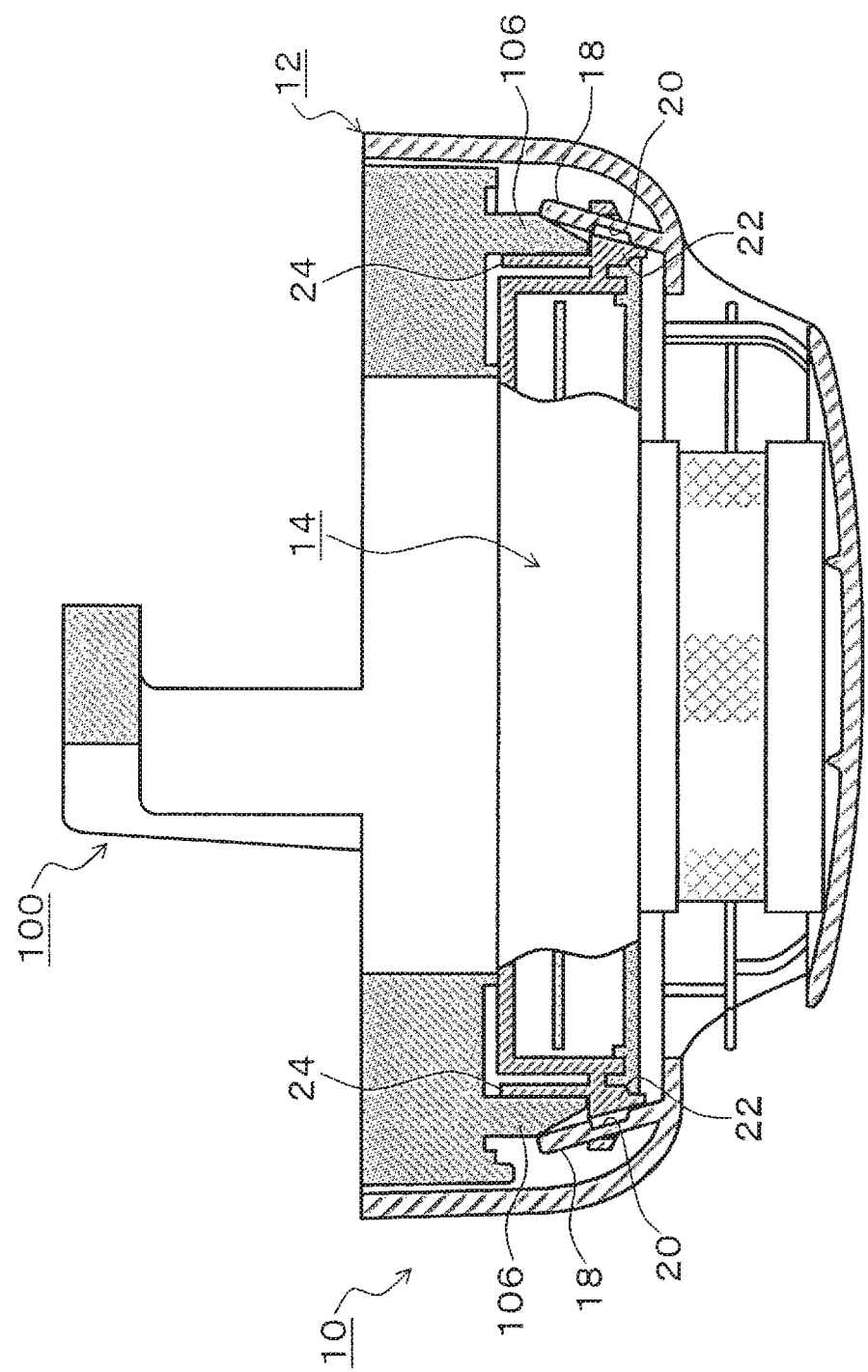
FIG. 12 is a view showing a state where the detachment tool is pushed into the sensor and an attachment structure is released.

FIG. 12 is a view showing a state where the detachment tool 100 is pushed into the sensor 10 and the attachment structure is released. When the detachment claw member 106 of the detachment tool 100 is pushed into the sensor while being guided by the guide rib 24, the fitting receiving member 18 which is provided to stand within the sensor cover 12 is deformed so as to be pushed down outwardly by the taper surface of the detachment claw member 106, the fitting concave section 20 on the inside of the fitting receiving member 18 is drawn and removed from the fitting claw member 22 of the sensor main body 14, and the fitting in the attachment structure is released.

FIG. 13 is a view showing a state where the sensor main body 14 is taken out from the sensor cover 12 by the detachment tool 100. As shown in FIG. 12, by pushing the detachment tool 100 into the sensor 10 to release the attachment of the sensor main body 14 to the sensor cover 12 and subsequently drawing up the detachment tool 100 in an upper direction of the drawing, it is possible to take out the sensor main body 14 in a state where the sensor main body 14 is connected to the downside of the detachment tool 100.

As described above, by a simple one-touch operation in which the detachment tool 100 is pushed into the sensor 10 and drawn up, it is possible to disassemble the sensor 10 and to simply detach the sensor main body 14 from the inside of the sensor cover 12.

(Connection and Connection Release Between Detachment Tool and Sensor Main Body)

FIG. 14 is a view showing a situation in which the detachment tool 100 is pushed into the sensor 10 with respect to a connection position with the sensor main body 14. When the detachment claw member 106 of the detachment tool 100 is positioned to and pushed into the sensor 10 as shown in FIG. 11, the connection receiving member 108 of the detachment tool 100 is in a position opposing the connection claw member 26 of the sensor main body 14 attached to the inside of the sensor cover 12 as shown in FIG. 14.

Figure 15:
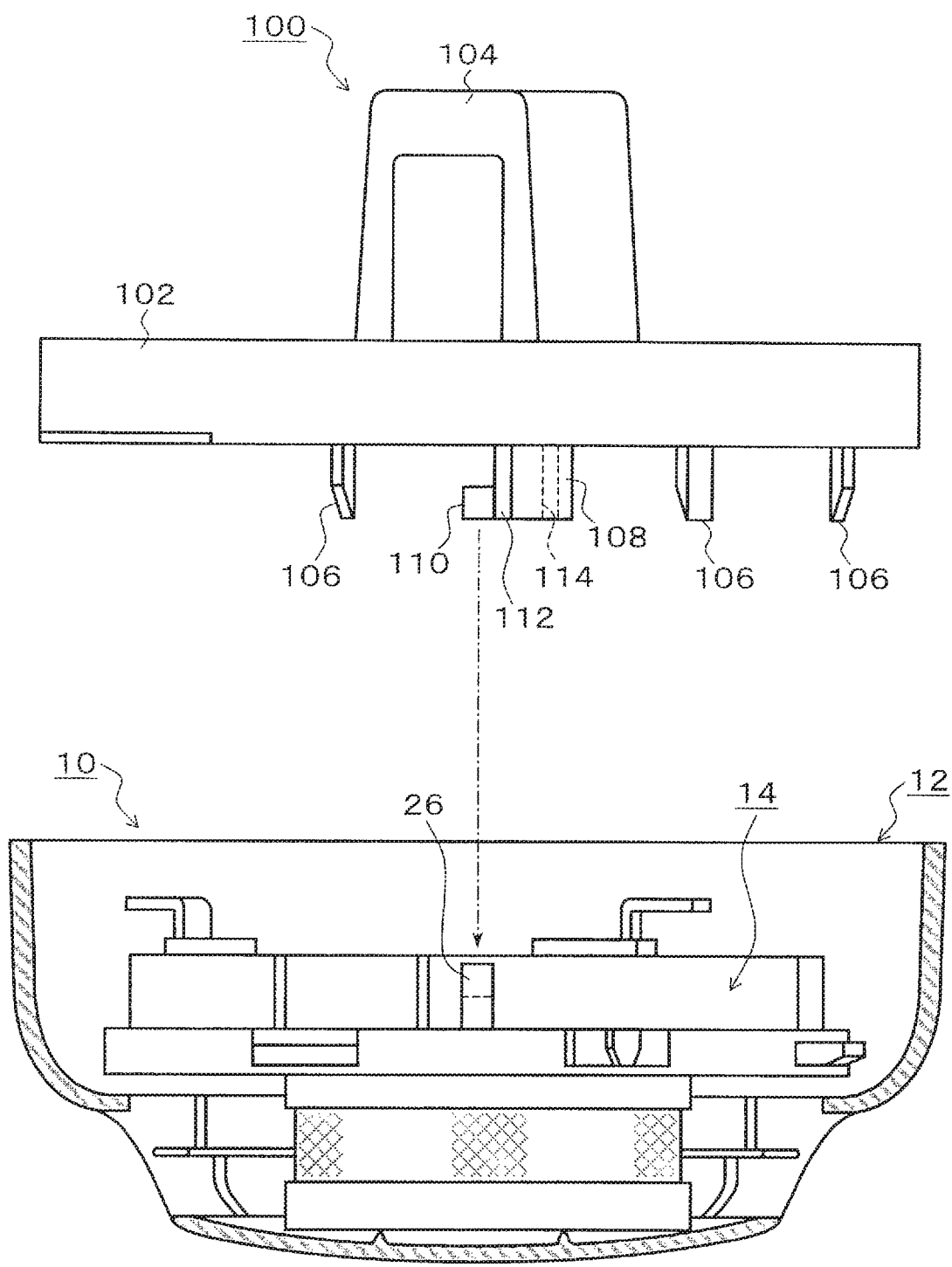
FIG. 15 is a view showing the situation in which the detachment tool is pushed into the sensor looking from a lateral side of FIG. 14.

FIG. 15 is a view showing a situation in which the detachment tool 100 is pushed into the sensor 10 looking from a lateral side of FIG. 14. The connection receiving section 110 in a cantilever form which is provided on the tip portion of the connection receiving member 108 which is provided on the downside of the detachment tool 100 opposes the connection claw member 26 which is provided to stand on the sensor main body 14.

Figure 16:
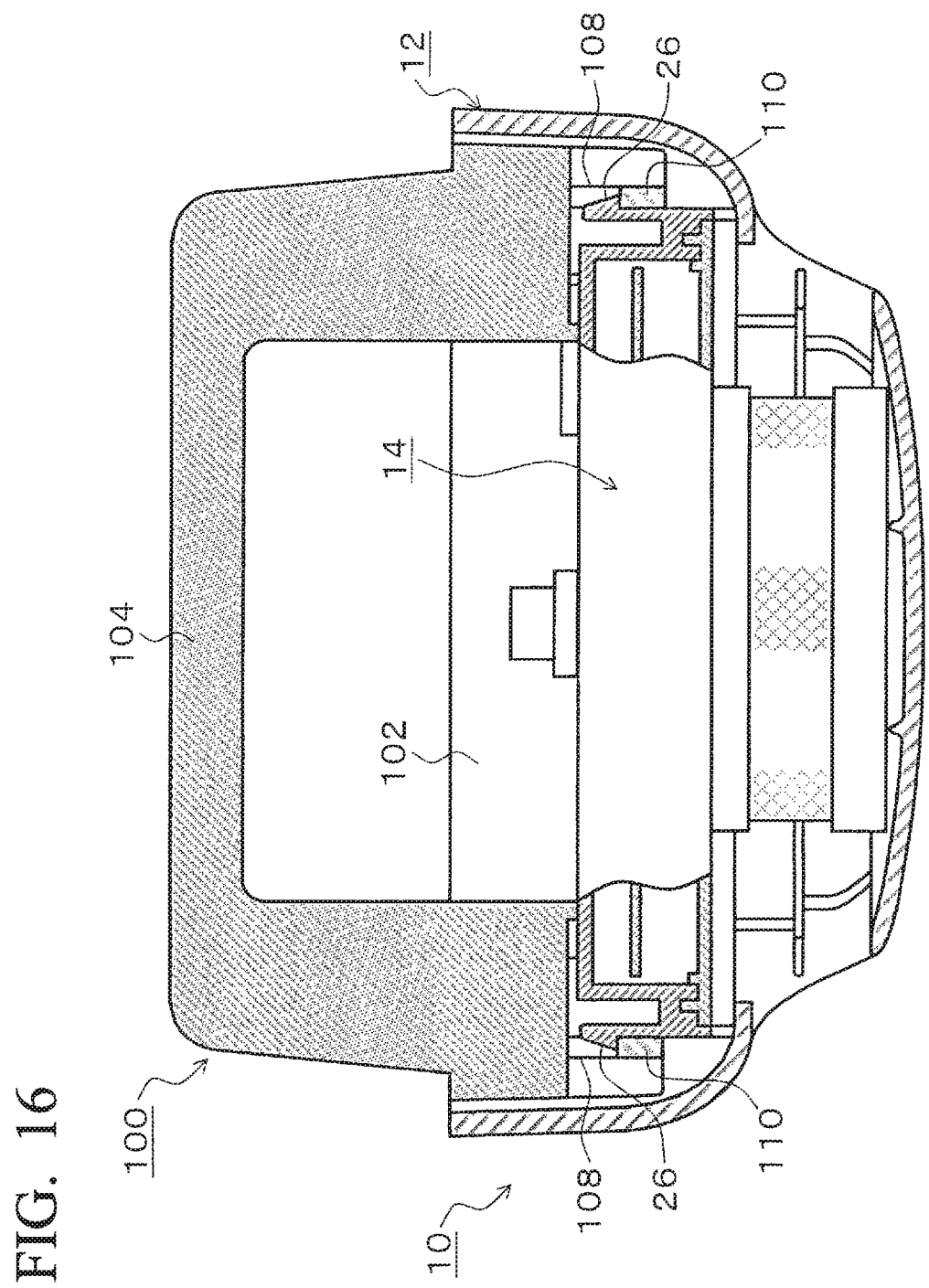
FIG. 16 is a view showing a state where the detachment tool is pushed into the sensor and connected to the sensor main body.

In this positioning state shown in FIG. 14 and FIG. 15, by pushing the detachment tool 100 into the sensor 10, as shown in FIG. 16, the connection receiving section 110 formed on the connection receiving member 108 of the detachment tool 100 fits the connection claw member 26 which is provided to stand on the sensor main body 14. In this case, as shown in FIG. 12, since the attachment of the sensor main body 14 to the sensor cover 12 is released by the detachment claw member 106 of the detachment tool 100, as shown in FIG. 17, by drawing up the detachment tool 100, it is possible to take out the sensor main body 14 from the sensor cover 12 in a state where the sensor main body 14 is connected to and held by the downside of the detachment tool 100.

Subsequently, in a state where the sensor main body 14 is held by hand and stabilized, by rotating the detachment tool 100 in a counterclockwise direction looking from the upside, the connection receiving section 110 (refer to FIG. 15) of the detachment tool 100 which is pushed into and thereby fits the connection claw member 26 of the sensor main body 14 is disconnected from the connection claw member 26 corresponding to the rotation of the detachment tool 100 to release the connection (refer to FIG. 15 regarding a disconnection direction of the connection receiving section 110), and the sensor main body 14 can be detached from the detachment tool 100.

Modified Example of Present Invention

Note that, the above embodiment is described using an example in which a scattered-light smoke detection structure is provided on the sensor main body 14; however, a structure in which heat or CO accompanied by a fire is detected may be provided.

In addition, in the connection structure between the attachment tool and the sensor main body 14, the connection receiving section 110 which is provided on the tip portion of the connection receiving member 108 as the cantilever form is set to an inverse L shape; however, may be set to an L shape. In this case, the rotation direction to release the connection between the detachment tool and the sensor main body 14 is an opposite direction compared to the case of the inverse L shape.

In addition, in the attachment structure between the sensor cover 12 and the sensor main body 14 in the above embodiment, the fitting receiving member 18 is provided on the sensor cover 12 and the fitting claw member 22 is provided on the sensor main body; however, on the contrary, the fitting claw member 22 may be provided on the sensor cover 12 and the fitting receiving member 18 may be provided on the sensor main body 14 in the attachment structure.

Similarly, with respect to the connection structure between the detachment tool 100 and the sensor main body 14, the connection receiving member 108 is provided on the detachment tool 100 and the connection claw member 26 is provided on the sensor main body 14 in the above embodiment; however, on the contrary, the connection claw member 26 may be provided on the detachment tool 100 and the connection receiving member 108 may be provided on the sensor main body 14 in the connection structure.

In addition, the above embodiment describes an embodiment of the sensor system configured by the sensor 10 and the detachment tool 100; however, the above embodiment describes, at the same time, an embodiment of a sensor and an embodiment of a detachment tool targeted by the present invention.

Additions, omissions, substitutions, and other modifications can be made without departing from the scope of the present invention. The invention is not to be considered as being limited by the foregoing description, is neither limited by the numbers provided in the foregoing description, and is only limited by the scope of the appended claims.

INDUSTRIAL APPLICABILITY

According to the sensor system of the present invention, with respect to the sensor including the attachment structure in consideration of disassembly in which the sensor main body is detachably attached to the inside of the sensor cover, it is possible to disassemble the sensor and to simply and easily detach the sensor main body from the sensor cover by a one-touch operation to push the detachment tool from the opening of the sensor cover into the sensor main body which is installed on the inside and is fixed.

DESCRIPTION OF THE REFERENCE SYMBOLS

10: SENSOR
12: SENSOR COVER
14: SENSOR MAIN BODY
14a: CIRCUIT STORAGE SECTION
14b: SMOKE DETECTION SECTION
15: CIRCUIT SUBSTRATE
16: SMOKE FLOW INLET
17: INSECT NET
18: FITTING RECEIVING MEMBER
20: FITTING CONCAVE SECTION
22: FITTING CLAW MEMBER
24: GUIDE RIB
25: MARKER
26: CONNECTION CLAW MEMBER
27: BASE POSITIONING RIB
28: POSITIONING GROOVE
30: GUIDE FRAME
32: TERMINAL METAL PART
34: POSITIONING RIB
100: DETACHMENT TOOL
102: TOOL MAIN BODY
104: HANDLE
105: MARKER
106: DETACHMENT CLAW MEMBER
108: CONNECTION RECEIVING MEMBER
110: CONNECTION RECEIVING SECTION
112: OUTWARD GUIDE RIB
114: INWARD GUIDE RIB

The invention claimed is:

1. A sensor system comprising:
a sensor that is provided with a sensor cover having an opening formed on one end and a sensor main body which is detachably disposed on an inner portion of the sensor cover; and
a detachment tool used to detach the sensor main body from the sensor cover, wherein
the sensor comprises an attachment structure used to attach the sensor main body to the inner portion of the sensor cover, the detachment tool comprises a detachment structure used to detach the sensor main body from the inner portion of the sensor cover, and in the detachment structure, by pushing the detachment tool into the sensor main body from the opening of the sensor cover, the sensor main body is detached from the inner portion of the sensor cover, and wherein the sensor system comprises a connection structure that detachably connects the detachment tool and the sensor main body when an attachment between the sensor cover and the sensor main body by the attachment structure of the sensor is released by the pushing of the detachment tool.

2. The sensor system according to claim 1, wherein
the attachment structure of the sensor comprises:
a fitting receiving member that is provided on the inner portion of the sensor cover and extends toward the opening of the sensor cover; and
a fitting claw member that is provided on the sensor main body and fits the fitting receiving member when the sensor main body is inserted to an attachment position of the inner portion of the sensor cover, and
the detachment structure of the detachment tool comprises:
a detachment claw member that is pushed into between the fitting receiving member and the fitting claw member and thereby releases a fitting state between the fitting receiving member and the fitting claw member.

3. The sensor system according to claim 1, wherein
the connection structure comprises:
a connection claw member provided on the sensor main body; and
a connection receiving member provided on the detachment tool, and wherein
the connection claw member is fitted and connected to the connection receiving member when the detachment tool is pushed into the sensor main body, and
a connection state between the connection claw member and the connection receiving member is released by rotating the detachment tool relative to the sensor main body.

4. The sensor system according to claim 3, wherein
the connection receiving member of the detachment tool comprises a connection receiving section of a cantilever structure extending to have a tip portion in an inverse L shape or an L shape,
the connection claw member is fitted and connected to the connection receiving section when the detachment tool is pushed into the sensor main body, and
a connection state between the connection claw member and the connection receiving member is released by rotating the detachment tool relative to the sensor main body.

5. A sensor comprising:
a sensor cover having an opening formed on one end;
a sensor main body disposed on an inner portion of the sensor cover; and
an attachment structure used to detachably attach the sensor main body to the inner portion of the sensor cover, wherein
by pushing a detachment tool from the opening of the sensor cover into the sensor main body disposed on the inner portion, an attachment by the attachment structure is released, and
the sensor comprises a connection structure that detachably connects the detachment tool and the sensor main body when the detachment tool is pushed and an attachment between the sensor cover and the sensor main body by the attachment structure is released.

6. The sensor according to claim 5, wherein
the attachment structure of the sensor comprises:
a fitting receiving member that is provided on the inner portion of the sensor cover and extends toward the opening of the sensor cover; and
a fitting claw member that is provided on the sensor main body and fits the fitting receiving member when the sensor main body is inserted to an attachment position of the inner portion of the sensor cover.

* * * * *